US011980471B2

(12) United States Patent
Kwon et al.

(10) Patent No.: US 11,980,471 B2
(45) Date of Patent: May 14, 2024

(54) PORTABLE ECG MEASURING DEVICE

(71) Applicant: VUNO Inc., Seoul (KR)

(72) Inventors: Oyeon Kwon, Seoul (KR); Woong Bae, Seoul (KR); Yeha Lee, Hwaseong-si (KR)

(73) Assignee: VUNO Inc., Seoul (KR)

( * ) Notice: Subject to any disclaimer, the term of this patent is extended or adjusted under 35 U.S.C. 154(b) by 323 days.

(21) Appl. No.: 17/330,102

(22) Filed: May 25, 2021

(65) Prior Publication Data

US 2021/0369172 A1  Dec. 2, 2021

(30) Foreign Application Priority Data

May 29, 2020 (KR) .................. 10-2020-0065016
Jul. 31, 2020 (KR) .................. 10-2020-0096232

(51) Int. Cl.
A61B 5/332 (2021.01)
A61B 5/00 (2006.01)
A61B 5/28 (2021.01)

(52) U.S. Cl.
CPC ............ *A61B 5/332* (2021.01); *A61B 5/0006* (2013.01); *A61B 5/28* (2021.01); *A61B 5/7221* (2013.01)

(58) Field of Classification Search
None
See application file for complete search history.

(56) References Cited

U.S. PATENT DOCUMENTS

| 4,865,039 | A | * | 9/1989 | Dunseath, Jr. | A61B 5/25 600/397 |
| 5,813,979 | A | * | 9/1998 | Wolfer | A61B 5/303 600/508 |
| 5,967,994 | A | * | 10/1999 | Wang | A61B 5/7221 600/509 |
| 6,119,035 | A | * | 9/2000 | Wang | A61B 5/318 600/509 |
| 8,954,129 | B1 | * | 2/2015 | Schlegel | A61B 5/282 600/382 |
| 9,649,042 | B2 | | 5/2017 | Albert et al. | |
| 10,413,251 | B2 | * | 9/2019 | Golda | A61B 5/08 |
| 10,905,891 | B2 | | 2/2021 | Kim | |
| 11,622,722 | B2 | * | 4/2023 | Acquista | H05K 1/189 600/391 |

(Continued)

FOREIGN PATENT DOCUMENTS

JP H05-329123 A 12/1993
KR 10-2009-0110438 A 10/2009

(Continued)

*Primary Examiner* — Kennedy Schaetzle
(74) *Attorney, Agent, or Firm* — Seed IP Law Group LLP

(57) ABSTRACT

Disclosed is a portable electrocardiogram measuring device for calculating one or more electrocardiogram leads according to an embodiment of the present disclosure. The device may include: a main measurement unit comprising a first electrode, a second electrode, and one or more processors; and a sub measurement unit comprising a third electrode, in which the one or more processors measure an electrocardiogram, by receiving electrical signals from at least two electrodes in a measurable state and by calculating different types of electrocardiogram leads based on the number of electrodes in the measurable state and an attachment position of electrodes.

13 Claims, 8 Drawing Sheets

(56) References Cited

U.S. PATENT DOCUMENTS

| | | | |
|---|---|---|---|
| 2004/0254435 A1* | 12/2004 | Mathews | A61B 5/25 600/372 |
| 2006/0030782 A1* | 2/2006 | Shennib | A61B 5/318 600/509 |
| 2015/0073285 A1 | 3/2015 | Albert et al. | |
| 2015/0157219 A1* | 6/2015 | Lee | A61B 5/02055 600/393 |
| 2018/0020937 A1* | 1/2018 | Chou | A61B 5/291 600/301 |
| 2019/0015004 A1 | 1/2019 | Maurizi et al. | |
| 2019/0082993 A1 | 3/2019 | Choi et al. | |
| 2019/0142294 A1* | 5/2019 | Govari | A61B 5/6801 257/307 |
| 2020/0069206 A1* | 3/2020 | Zaliasl | A61B 5/276 |

FOREIGN PATENT DOCUMENTS

| | | | |
|---|---|---|---|
| KR | 10-1889747 B1 | 8/2018 | |
| KR | 10-2019-0008133 A | 1/2019 | |
| KR | 10-2019-0032088 A | 3/2019 | |
| KR | 10-1995153 B1 | 7/2019 | |
| WO | WO-9009143 A1 * | 8/1990 | ........... A61B 5/0402 |
| WO | WO-2016070663 A1 * | 5/2016 | ........... A61B 5/0402 |
| WO | WO-2020002133 A1 * | 1/2020 | |
| WO | WO-2020259725 A1 * | 12/2020 | ............. A61B 5/303 |

\* cited by examiner

PORTABLE ECG MEASURING DEVICE

CROSS-REFERENCE TO RELATED APPLICATIONS

This application claims priority to and the benefit of Korean Patent Application No. 10-2020-0065016 filed in the Korean Intellectual Property Office on May 29, 2020, and Korean Patent Application No. 10-2020-0096232 filed in the Korean Intellectual Property Office on Jul. 31, 2020 the entire contents of which are incorporated herein by reference.

BACKGROUND

Technical Field

The present disclosure relates to an electrocardiogram measuring device, and more particularly, to a portable electrocardiogram measuring device measuring electrocardiogram according to a measurable state of an electrode.

Description of the Related Art

Electrocardiogram (ECG) measures and records electrical activity current according to contraction and extension of heart muscle. An activity potential that is generated when the heart muscle contracts and relaxes causes current spreading from the heart to an entire body, and the current generates a potential difference according to the state of the body, and the potential difference is detected through a surface electrode attached to the skin of the human body. The electrocardiogram is used to check whether the heart is abnormal, and an indicator basically considered to diagnose a cardiovascular disease, such as angina, myocardial infarction, and arrhythmia.

Meanwhile, ECG devices of a wearable type (clock type, patch type, or pad type), which are portable in the art, are mostly measuring only a single lead signal, and only very few companies measure a signal which exceeds a single lead.

Korean Patent No. 10-1995153B1 discloses "Method for Compensation of ECG Signal of Wearable Device Using Acceleration Sensor and ECG Measurement Wearable Device Adopting Same."

BRIEF SUMMARY

The inventors of the present disclosure have appreciated and identified that even in the case of using a single lead in the related art, the corresponding ECG device has to be closely attached to the skin of a specific portion of a lower body. The inventors have realized that not only is the measurement posture uncomfortable to a patient but also the received signal from the patient is unstable.

Accordingly, the inventors have recognized that there is a continuous demand for portable electrocardiogram measurement devices that can measure the number of leads exceeding a single lead and simultaneously provide a relatively accurate measurement result.

One or more embodiments of the present disclosure have been made in an effort to provide a more accurate measurement result by providing a portable ECG measuring device for measuring ECG according to a measurable state of an electrode.

An embodiment of the present disclosure provides a portable electrocardiogram measuring device for calculating one or more electrocardiogram leads. The device may include: a main measurement unit comprising a first electrode, a second electrode, and one or more processors; and a sub measurement unit comprising a third electrode, in which the one or more processors measure an electrocardiogram, by receiving electrical signals from at least two electrodes in a measurable state and by calculating different types of electrocardiogram leads based on the number of electrodes in the measurable state and attachment positions of electrodes.

In an alternative embodiment, the one or more processors may determine whether each electrode is in a measurable state based on a quality of an electrical signal received from the electrodes.

In an alternative embodiment, the quality of the electrical signal may include at least one of a strength of the electrical signal, a waveform of the electrical signal, or an input time interval of the electrical signal.

In an alternative embodiment, the third electrode may be at least one of a dry type electrode or a wet type electrode.

In an alternative embodiment, the portable ECG measuring device may further include one or more cables, the main measurement unit may include one or more terminal insertion units for wired connection, and the cable may include a terminal for wired connection on one end, and the other end may be connected to the sub measurement unit including the third electrode.

In an alternative embodiment, the portable ECG measuring device may further include a rotating unit for storing the cable.

In an alternative embodiment, each of the main measurement unit and the sub measurement unit may include a network unit for wireless data communication, and the main measurement unit and the sub measurement unit may wirelessly transmit and receive data.

In an alternative embodiment, the sub measurement unit may be capable of being coupled to one side of the main measurement unit through at least one of coupling by magnetic force, coupling by adhesive force, or fitting coupling.

In an alternative embodiment, the main measurement unit may be capable of storing the sub measurement unit.

In an alternative embodiment, the one or more processors may determine that the third electrode is in a non-measurable state when the sub measurement unit comprising the third electrode is stored in the main measurement unit.

In an alternative embodiment, the one or more processors may calculate a changed type of electrocardiogram lead based on a changed number of electrodes which is in the measurable state or a changed attachment position of the electrodes, when the number of electrodes in the measurable state or the attachment position of the electrodes is changed during the electrocardiogram measurement.

In an alternative embodiment, when the number of electrodes in the measurable state is two, the ECG lead calculated by the processor is lead I if the attachment positions of two electrodes are the left arm (LA) and the right arm (RA), lead II if the attachment positions are the left leg (LL) and the right arm (RA), and lead III if the attachment positions are the left leg (LL) and the left arm (LA).

In an alternative embodiment, when the number of electrodes in the measurable state is three, the electrocardiogram lead calculated by the processors may include at least one of lead I, lead II, lead III, lead aVR, lead aVL, or lead aVF.

In an alternative embodiment, the portable ECG measuring device may further include an output unit, and the output unit may output at least one of information related to electrical signal measurement of each electrode, information related to an electrocardiogram measurement method of a processor, or user notification information.

According to an embodiment of the present disclosure, a portable ECG measuring device for measuring ECG according to a measurable state of an electrode can be provided.

DETAILED DESCRIPTION

Figure 1:
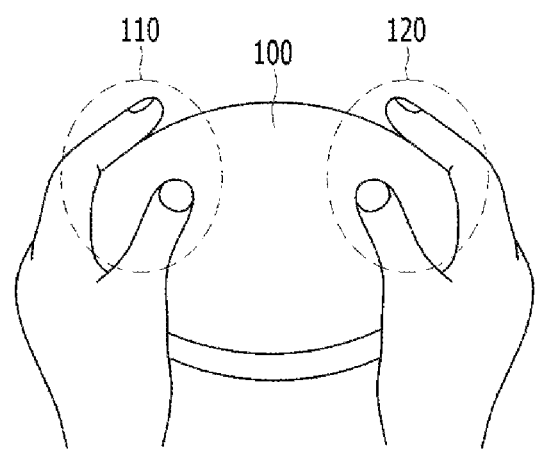
FIG. 1 is a diagram illustrating when a user uses a main measurement unit included in a portable electrocardiogram measuring device.

Various embodiments will now be described with reference to drawings. In the present specification, various descriptions are presented to provide appreciation of the present disclosure. However, it is apparent that the embodiments can be executed without the specific description.

"Component," "module," "system," and the like which are terms used in the specification refer to a computer-related entity, hardware, firmware, software, and a combination of the software and the hardware, or the execution of the software. For example, the component may be a processing process executed on a processor, the processor, an object, an execution thread, a program, and/or a computer, but is not limited thereto. For example, both an application executed in a computing device and the computing device may be the components. One or more components may reside within the processor and/or a thread of execution. One component may be localized in one computer. One component may be distributed between two or more computers. Further, the components may be executed by various computer-readable media having various data structures, which are stored therein. The components may perform communication through local and/or remote processing according to a signal (for example, data transmitted from another system through a network such as the Internet through data and/or a signal from one component that interacts with other components in a local system and a distribution system) having one or more data packets, for example.

The term "unit" may include any electrical circuitry, features, components, an assembly of electronic components or the like. That is, "unit" may include any processor-based or microprocessor-based system including systems using microcontrollers, integrated circuit, chip, microchip, reduced instruction set computers (RISC), application specific integrated circuits (ASICs), field-programmable gate arrays (FPGAs), graphical processing units (GPUs), logic circuits, and any other circuit or processor capable of executing the various operations and functions described herein. The above examples are examples only, and are thus not intended to limit in any way the definition or meaning of the term "unit."

In some embodiments, the various units described herein may be included in or otherwise implemented by processing circuitry such as a microprocessor, microcontroller, or the like.

The term "or" is intended to mean but inclusive "or." That is, when not separately specified or not clear in terms of a context, a sentence "X uses A or B" is intended to mean one of the natural inclusive substitutions. That is, the sentence "X uses A or B" may be applied to any of the case where X uses A, the case where X uses B, or the case where X uses both A and B. Further, it should be understood that the term "and/or" used in this specification designates and includes all available combinations of one or more items among enumerated related items.

It should be understood that the term "comprise" and/or "comprising" means presence of corresponding features and/or components. However, it should be appreciated that the term "comprises" and/or "comprising" means that presence or addition of one or more other features, components, and/or a group thereof is not excluded. Further, when not separately specified or it is not clear in terms of the context that a singular form is indicated, it should be construed that the singular form generally means "one or more" in this specification and the claims.

The term "at least one of A or B" should be interpreted to mean "a case including only A," "a case including only B," and "a case in which A and B are combined."

Those skilled in the art need to recognize that various illustrative logical blocks, configurations, modules, circuits, means, logic, and algorithm steps described in connection with the embodiments disclosed herein may be additionally implemented as electronic hardware, computer software, or combinations of both sides. To clearly illustrate the interchangeability of hardware and software, various illustrative components, blocks, constitutions, means, logic, modules, circuits, and steps have been described above generally in terms of their functionalities. Whether the functionalities are implemented as the hardware or software depends on a specific application and design restrictions given to an entire system. Skilled artisans may implement the described functionalities in various ways for each particular application. However, such implementation decisions should not be interpreted as causing a departure from the scope of the present disclosure.

The description of the presented embodiments is provided so that those skilled in the art of the present disclosure use or implement the present disclosure. Various modifications to the embodiments will be apparent to those skilled in the art. Generic principles defined herein may be applied to other embodiments without departing from the scope of the present disclosure. Therefore, the present disclosure is not limited to the embodiments presented herein. The present disclosure should be analyzed within the widest range which is coherent with the principles and new features presented herein.

Hereinafter, embodiments of the present disclosure will be described in more detail with reference to drawings. However, the present disclosure may be embodied as a lot of various forms, and should not be construed as being restricted to the embodiments described herein.

A portable electrocardiogram (ECG) measuring device for calculating one or more ECG leads according to an embodiment of the present disclosure may include a main measurement unit including a first electrode, a second electrode, and one or more processors, and a sub measurement unit including a third electrode. The electrode may be configured as at least one electrode of a dry type electrode or a wet type electrode. The electrode is closely attached to the skin of a user to receive an electrical signal generated according to an electrical activity of the heart of the user. The electrical signal may include, for example, a potential measured in the skin. The processor may measure electrocardiogram (ECG) based on a potential difference received at least two or more electrodes.

In this specification, the word 'measurement' means measuring, calculating, acquiring, or computing the electrocardiogram lead as a result which becomes a final subject of clinical determination. The meaning of the measuring, the calculating, the acquiring, or the computing may include an operation of amplifying the received electrical signal or an operation of calculating a potential difference of two or more electrical signals. In this specification, since each electrode 'receives' the electrical signal, the reception should be distinguished from ECG 'measurement.' In this specification, the processor included in the portable ECG measuring device measures the ECG based on the received electrical signal.

FIG. 1 is a diagram illustrating when a user uses a main measurement unit included in a portable electrocardiogram measuring device.

The portable ECG measuring device according to an embodiment of the present disclosure may include a main measurement unit 100 illustrated in FIG. 1. The electrode layer 100 may include a first electrode 110 and a second electrode 120. The first electrode 110 and the second electrode 120 may be distinguished according to positions thereof. The first electrode 110 and the second electrode 120 may be distinguished according to a target body part of a user to be in close contact. The first electrode and the second electrode may constitute a part of a housing of the main measurement unit. When the first electrode and the second electrode constitute a part of the housing of the main measurement unit, the user may simultaneously possess or use two electrodes without a separate cable. As illustrated in FIG. 1, the main measurement unit 100 may be a circular pad shape as an embodiment. When the main measurement unit 100 has the circular pad shape, and the dry type first electrode 110 and second electrode 120 are located at both sides of a circular pad, the user may measure the ECG by holding the first electrode 110 and the second electrode 120 with a thumb and a forefinger, and closely attaching both arms strongly. An example of the shape of the main measurement unit described above is just an example, and does not limit the present disclosure.

Figure 2:
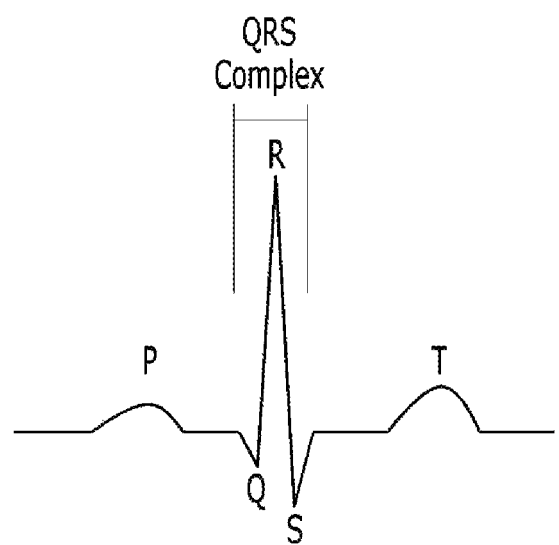
FIG. 2 is a graph showing electrocardiogram measured based on an electrical signal received from an electrode.

FIG. 2 is a graph showing electrocardiogram measured based on an electrical signal received from an electrode. As illustrated in FIG. 2, a waveform of the ECG may be distinguished into a P wave, a Q wave, an R wave, an S wave, and a T wave. First, the P wave as a waveform which appears when an atrium is depolarized progresses from the right to the left crossing the atrium. Accordingly, a front portion of the P wave represents depolarization of the right atrium and a rear portion of the P wave represents depolarization of the left atrium.

A QRS complex including the Q wave, the R wave, and the S wave is generated by depolarization of a ventricle. The Q wave represents depolarization of an inter-ventricle septum and remaining parts of the QRS complex represent depolarization of a left/right ventricle which simultaneously occurs.

The T wave is caused by repolarization of the ventricle. The T wave occurs at the end of a ventricular shrink period. The repolarization is slower than the depolarization, and is further widened and is lower in amplitude than the QRS complex. As described above, movement of an internal ventricle and the internal atrium of the heart may be known through the ECG measured based on the electrical signal received from the electrode.

The ECG lead included in ECG data is constituted by a total of 12 leads. The ECG lead may be divided into a limb lead and a precordial lead. The limb lead may be again divided into standard limb leads including lead I, lead II, and lead III, and augmented limb leads including lead aVR, lead aVL, and aVF. The standard limb lead corresponds to the standard lead. The augmented limb lead corresponds to the limb lead. The standard limb leads including three leads among 12 leads are bipolar leads recording a potential difference of two different electrodes. The remaining leads other than the standard limb lead among 12 leads are a unipolar lead measured based on one electrode.

Throughout this specification, inducement and lead may be interchanged and used, and all of the induction and the inducement and the lead refer to the lead included in the ECG data.

The portable ECG measuring device according to an embodiment of the present disclosure may include a third electrode in order to measure at least two leads by exceeding one lead. The third electrode can be either the dry type electrode or the wet type electrode. When the third electrode is the dry type electrode, there is an advantage in that the electrical signal is capable of being received only by closing attaching the third electrode included in the sub measurement unit to a part of the body without additional processing, and as a result, it is easy to measure the ECG. When the third electrode is the wet type electrode, the portable ECG measuring device has an advantage of receiving a more accurate electrical signal by adhering the third electrode to the skin. The portable ECG measuring device according to an embodiment of the present disclosure may additionally include a fourth electrode, a fifth electrode, etc., in order to measure the more accurate ECG.

The portable ECG measuring device according to an embodiment of the present disclosure may further include one or more cables, the main measurement unit may include one or more terminal inserting units for wired connection, and the cable may include a terminal for wired connection on one end, and the other end may be connected to the sub measurement unit including the third electrode. The terminal means a component used for accessing an electrical cable or an optical cable for communication. The terminal may include all types of terminals used for communication, such as a USB terminal, a TS terminal, a TRS stereo terminal, a TRRS stereo microphone terminal, etc. The terminal inserting unit may mean a terminal inserting unit which is compatible with the above-described terminal to receive data. The portable ECG measuring device according to an embodiment of the present disclosure may measure an additional lead by exceeding one lead in wired connection to an additional electrode other than the first electrode and the second electrode included in the main measurement unit.

Figure 3:
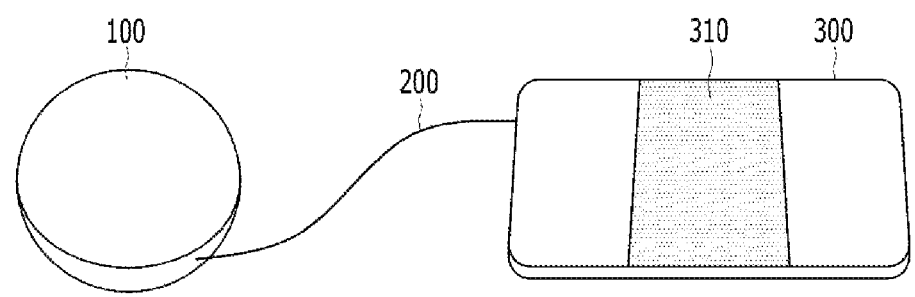
FIG. 3 is a diagram illustrating a portable electrocardiogram measuring device in which a main measurement unit and a sub measurement unit are wiredly connected.

FIG. 3 is a diagram illustrating a portable electrocardiogram measuring device in which a main measurement unit and a sub measurement unit are wiredly connected. As illustrated in FIG. 3, the sub measurement unit 300 may include a third electrode 310. The sub measurement unit 300 may be connected to the main measurement unit 100 through a cable 200. The sub measurement unit 300 may transmit the electrical signal received by the third electrode 310 to the processor of the main measurement unit 100 through the connection by the cable. In an embodiment of the present disclosure, the sub measurement unit 300 may be configured in a plate shape having a predetermined width or more, which may be laid on the floor to endure a predetermined pressure. When the sub measurement unit 300 is configured in the plate shape and includes the third electrode 310, the user may measure the ECG by closely attaching a sole of a left leg or a right leg, and the third electrode 310, and by gripping the main measurement unit 100 with both arms. When the sub measurement unit 300 is configured in the plate shape as described above and the ECG is measured while pressing the third electrode 310 with the leg, the user uses gravity as it is to closely attach the sole and the third electrode 310, thereby increasing adhesion without applying separate force. This allows the third electrode 310 to accurately receive the electrical signal, resulting in an effect of enhancing accuracy of the ECG measurement. An example of the shape or material of the sub measurement unit described above is just an example, and does not limit the present disclosure. The third electrode may be the wet type electrode. In this case, the user may also measure the ECG by attaching the sub measurement unit 300 including the wet type third electrode 310 to one region of a lower abdomen or one region of a leg and then gripping the main measurement unit 100 with both arms.

In an embodiment of the present disclosure, the portable ECG measuring device may further include a rotating unit for storing the cable. The rotating unit may include, for example, a reel, a spool, or a bobbin. The disclosure of the rotating unit described above is just an example and the present disclosure is not limited thereto. The cable may be wound around a central axis of the rotating unit in a predetermined direction and stored in the rotating unit. According to an embodiment of the present disclosure, when the portable ECG measuring device includes the rotating unit and stores the cable, there is an advantage that the user may adjust the number of electrodes for measuring the ECG as necessary without a constraint of a place. For example, when the user intends to measure a single ECG lead through two electrodes, the user may measure the ECG in a state in which the cable is wound on the rotating unit. On the contrary, when the user intends to measure a plurality of ECG leads through three electrodes, the user may release the cable from the rotating unit and attach the released cable to a desired body part, and measure the plurality of ECG leads.

In the portable ECG measuring device according to an embodiment of the present disclosure, each of the main measurement unit and the sub measurement unit may include a network unit for wireless data communication. The main measurement unit and the sub measurement unit may wirelessly transmit and receive data. The sub measurement unit may transmit the electrical signal received by the third electrode to the main measurement unit through the network unit. The data communication by the network unit may be performed by a short-range wireless communication method. The short-range wireless communication method may include, for example, a wireless LAN (WLAN), a Bluetooth method, and the like.

Figure 4:
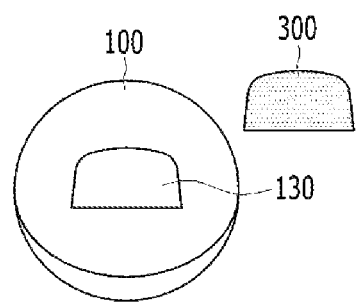
FIG. 4 is a diagram illustrating a portable electrocardiogram measuring device in which a main measurement unit and a sub measurement unit are wiredly connected.

FIG. 4 is a diagram illustrating a portable electrocardiogram measuring device in which a main measurement unit and a sub measurement unit are wiredly connected. As illustrated in FIG. 4, the sub measurement unit 300 may be wirelessly connected to the main measurement unit 100 without the cable. A part of a housing of the sub measurement unit 300 may be constituted by the third electrode. Further, an entire surface of the sub measurement unit 300 may also be constituted by the third electrode in order to broaden a contact area between the body part of the user and the third electrode. The sub measurement unit 300 may include the network unit and may be manufactured in the plate shape illustrated in FIG. 2. In this case, the user may measure the ECG by gripping the main measurement unit 100 with both arms while pressing a wireless plate with the sole. The sub measurement unit 300 has an advantage in that a separate cable is not required when the sub measurement unit 300 includes the network unit for the wireless communication. In an embodiment of the present disclosure, the user may attach the sub measurement unit 300 to one area 130 of the main measurement unit 100. For example, when both the first electrode and the second electrode are located on one surface of the main measurement unit 100 as illustrated in FIG. 1, one area 130 to which the sub measurement unit 300 is attached may be a back surface of the one surface. In other words, in the main measurement unit having a thin pad type 3D shape, when the first and second electrodes are located on the front surface, the sub measurement unit may be attached onto the rear surface. When the sub measurement unit are attached onto an opposite surface of the positions of the first and second electrodes, the user grips the first and second electrodes of the main measurement unit 100 with both arms, respectively, and attaches the sub measurement unit 300 of the rear surface onto one surface of the leg or abdomen to acquire two or more ECG leads.

In the portable electrocardiogram measuring device according to an embodiment of the present disclosure, the sub measurement unit is capable of being coupled to one side of the main measurement unit through at least one of coupling by magnetic force, coupling by adhesive force, or fitting coupling. The user may measure the ECG by coupling the sub measurement unit to the main measurement unit through the coupling and gripping the first and second electrodes included in the main measurement unit with both arms and then contacting the third electrode included in the sub measurement unit with a part of the surface of the leg or the body. Further, the user may freely move the third electrode included in the sub measurement unit through the separation and contact the third electrode with a part of the surface of the body. In this case, it is not necessary to take an unstable posture for measuring the ECG. Furthermore, the user may modify a form according to a symbol through the sub measurement unit and the main measurement unit which are capable of being coupled or separated. In other words, the user may couple the main measurement unit and the sub measurement unit in order to make carrying convenient according to the symbol and separate the main measurement unit and the sub measurement unit in order to make measurement convenient.

In an embodiment of the present disclosure, the coupling may be fitting coupling. The main measurement unit having the 3D shape may include a coupling structure for the main measurement unit to be fitting-coupled with the sub measurement unit on one surface. The coupling structure for the fitting coupling may be a fitting groove with a size to accommodate a thickness of the sub measurement unit. The fitting groove may be configured on one surface of the main measurement unit so as to be intersected and fastened to the sub measurement unit. When being coupled and then separated, the user removes a coupling portion of the sub measurement unit fastened to the fitting groove of the main measurement unit to separate the main measurement unit and the sub measurement unit. The shape of the sub measurement unit may form the coupling portion and may be fitting coupled onto one surface of the main measurement unit.

In another embodiment, the coupling may be achieved by adhesion. The main measurement unit having the 3D shape may include a surface for being adhesion-coupled to a part of one surface. The surface for being adhesion-coupled may have a predetermined adhesive strength. The predetermined adhesive strength as a physical amount determined by the user may refer to a strength enough for the coupling portion of the sub measurement unit, which is adhered and coupled not to be easily separated from the main measurement unit. The sub measurement unit may include the coupling portion on one surface so as to be adhered to correspond to a coupled portion of the main measurement unit. When coupling and separating, the user may separate the adhered and coupled sub measurement unit by giving force having a predetermined magnitude. A means for the adhesion coupling may include, for example, a Velcro, a putty, a tape, and the like.

In another embodiment, the coupling may be a coupling by magnetic force. The main measurement unit may include a magnet which allows a specific pole (e.g., an N pole) to face the surface on one surface. The sub measurement unit may include a pole (e.g., an S pole) that is opposite to and correspond to the magnet included in the main measurement unit. The sub measurement unit may be attached or coupled to one surface of the main measurement unit by the magnetic force between the magnets. The user may also separate the main measurement unit and the sub measurement unit as necessary by giving force equal to or more than a magnitude of attraction by the magnetic force.

An example of the type of coupling described above is just an example, and includes all types of coupling methods in which the main measurement unit and the sub measurement unit may be coupled. According to the present disclosure, the user may perform coupling or separation according to a situation of the user, and adjust whether to use the third electrode included in the sub measurement unit or change an attachment position of the third electrode to the body.

In the portable ECG measuring device according to an embodiment of the present disclosure, the main measurement unit may store the sub measurement unit. In the present disclosure, the main measurement unit possesses a space for storing the sub measurement unit to easily keep the sub measurement unit including the third electrode when the third electrode is not used. For example, the 3D-shaped main measurement unit may include an empty space having a volume of the sub measurement unit or more therein. The empty space may be a space for storing the sub measurement unit. The empty space may be covered with a separate cover which occupies one area of the surface of the main measurement unit while contacting the surface of the main measurement unit. The cover may be opened or closed while being completely separated from the other surface of the main measurement unit. The cover may be opened or closed in connection with a specific point of the other surface of the main measurement unit. A connection method of the cover and the other surface of the main measurement unit may be, for example, a connection method through a hinge. Further, in another embodiment, the 3D-shaped main measurement unit may include a protruded space for storing the sub measurement unit on one surface. An example of the storing space described above is just an example, and does not limit the present disclosure.

When the sub measurement unit may be stored in the main measurement unit as described above, the user may possess the third electrode even when not using the third electrode for measuring the ECG. This has an advantage in that when more accurate ECG measurement is required by adding the third electrode, the user may use the third electrode without receiving a constraint of time and place. Further, in some embodiments, in the case of a sub measurement unit of a wireless connection method, the sub measurement unit requires a battery for the wireless data communication, and the user may also charge the battery of the sub measurement unit simultaneously with storing the battery.

The processor included in the portable ECG measuring device according to an embodiment of the present disclosure may receive the electrical signal from at least two electrodes in the measurable state and measure the ECG, and calculate different types of ECG leads based on the number of electrodes in the measurable state and attachment positions of the electrodes.

Figure 5:
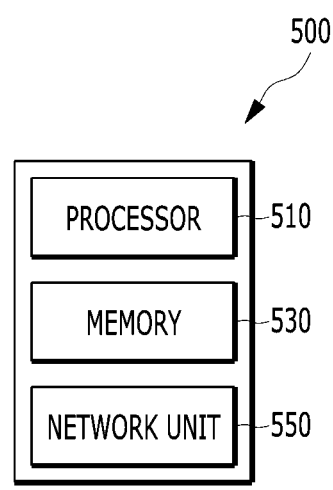
FIG. 5 is a block diagram of a computing device which the main measurement unit includes to measure electrocardiogram according to an embodiment of the present disclosure.

FIG. 5 is a block diagram of a computing device which the main measurement unit includes to measure electrocardiogram according to an embodiment of the present disclosure. A configuration of the computing device 500 illustrated in FIG. 5 is only an example shown through simplification. In an embodiment of the present disclosure, the computing device 500 may include other components for performing a computing environment of the computing device 500 and only some of the disclosed components may constitute the computing device 500.

The computing device 500 may include a processor 510, a memory 530, and a network unit 550.

The processor 510 may be constituted by one or more cores and may include processors for data analysis and deep learning, which include a central processing unit (CPU), a general purpose graphics processing unit (GPGPU), a tensor processing unit (TPU), and the like of the computing device. The processor 510 may read a computer program stored in the memory 530 to perform data processing for machine learning according to an embodiment of the present disclosure. According to an embodiment of the present disclosure, the processor 510 may perform a calculation for learning the neural network. The processor 510 may perform calculations for learning the neural network, which include processing of input data for learning in deep learning (DL), extracting a feature in the input data, calculating an error, updating a weight of the neural network using backpropagation, and the like. At least one of the CPU, GPGPU, and TPU of the processor 510 may process learning of a network function. For example, both the CPU and the GPGPU may process the learning of the network function and data classification using the network function. Further, in an embodiment of the present disclosure, processors of a plurality of computing devices may be used together to process the learning of the network function and the data classification using the network function. Further, the computer program executed in the computing device according to an embodiment of the present disclosure may be a CPU, GPGPU, or TPU executable program.

According to an embodiment of the present disclosure, the memory 530 may store any type of information generated or determined by the processor 510 or any type of information received by the network unit 550.

According to an embodiment of the present disclosure, the memory 530 may include at least one type of storage medium of a flash memory type storage medium, a hard disk type storage medium, a multimedia card micro type storage medium, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The computing device 500 may operate in connection with a web storage performing a storing function of the memory 530 on the Internet. The description of the memory is just an example and the present disclosure is not limited thereto.

The network unit 550 according to an embodiment of the present disclosure may use various wired communication systems such as public switched telephone network (PSTN), x digital subscriber line (xDSL), rate adaptive DSL (RADSL), multi rate DSL (MDSL), very high speed DSL (VDSL), universal asymmetric DSL (UADSL), high bit rate DSL (HDSL), and local area network (LAN).

The network unit 550 presented in this specification may use various wireless communication systems such as code division multi access (CDMA), time division multi access (TDMA), frequency division multi access (FDMA), orthogonal frequency division multi access (OFDMA), single carrier-FDMA (SC-FDMA), and other systems.

In the present disclosure, the network unit 550 may be configured regardless of communication modes such as wired and wireless modes and may be part of various communication networks including a personal area network (PAN), a wide area network (WAN), and the like. Further, the network may be known World Wide Web (WWW) and may adopt a wireless transmission technology used for short-distance communication, such as infrared data association (IrDA) or Bluetooth.

The techniques described in this specification may also be used in other networks in addition to the aforementioned networks.

In an embodiment of the present disclosure, the portable ECG measuring device may include a network unit 550 and measure the ECG through communication with an external server or computing device. The external server or computing device may be, for example, a PC, a tablet, or a smartphone terminal. The communication may include wired/wireless communication. When measuring the ECG through the communication with the external server as described above, the portable ECG measuring device according to the present disclosure transmits the electrical signal received from one or more electrodes to the external server to reduce a burden of a computation and lower a burden of power consumption.

Throughout this specification, the "measurable state" meaning the state of the electrode means the state of the electrode which the processor determines based on the electrical signal received from the electrode. When the processor examines an electrical signal received from a specific electrode and classifies the examined electrical signal into a normal electrical signal, the processor may determine the corresponding electrode as the measurable state. In this case, the processor may insert the electrical signal received from the corresponding electrode into an ECG measurement process and calculate an ECG measurement result. When the processor classifies the electrical signal received from the specific electrode into an abnormal electrical signal, the processor may determine the corresponding electrode as a non-measurable state. In this case, even though the processor receives the electrical signal from the corresponding electrode, the processor may disregard the received electrical signal and calculate the ECG measurement result based on another electrode. The method for determining the state of the electrode based on the electrical signal will be described below in detail.

In this specification, the "ECG measurement" may include a case where the processor calculates or records the ECG lead by computing the electrical signal received from one or more electrodes. The method for calculating the ECG lead may vary depending on the number of electrodes or the attachment position of the electrode to the body part. Hereinafter, the ECG measurement method will be described with reference to FIGS. 6 and 7.

Figure 6:
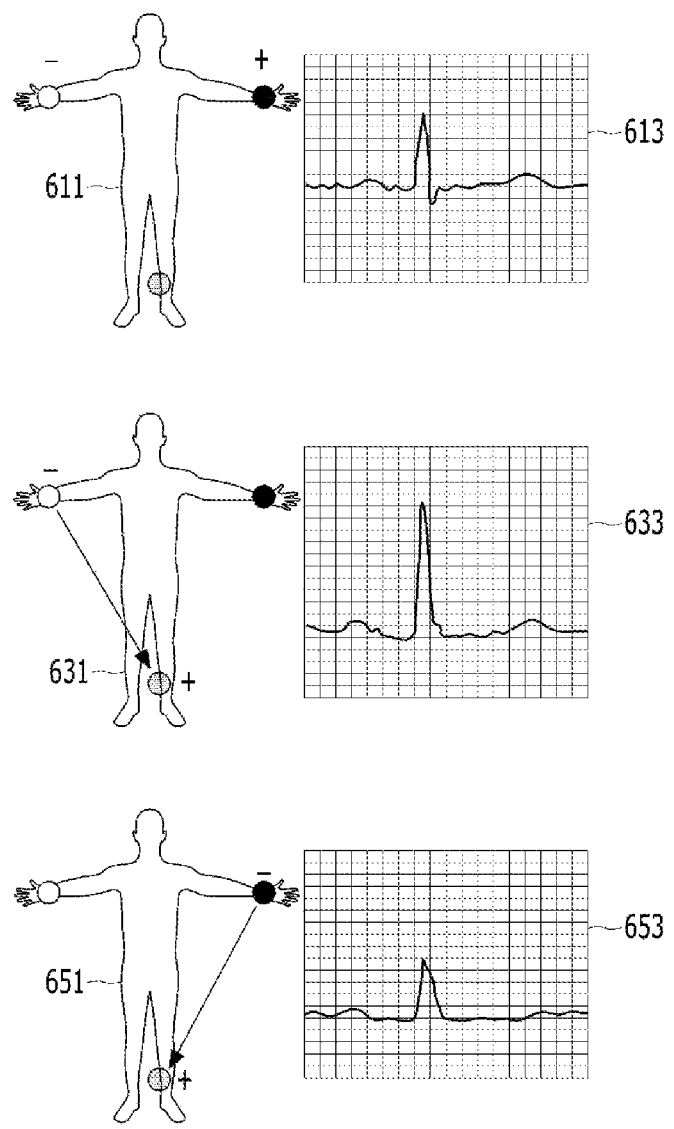
FIG. 6 is a diagram illustrating a standard limb lead among electrocardiogram leads that may be measured according to an embodiment of the present disclosure.

FIG. 6 is a diagram illustrating a standard limb lead among electrocardiogram leads that may be measured according to an embodiment of the present disclosure. In the case of measurement 611 of lead I, lead I is measured by calculating a potential difference of both electrodes by setting the right arm to a negative (−) pole and the left arm to a positive (+) pole. Reference numeral 613 of FIG. 6 represents a waveform of lead I. In the case of measurement 631 of lead II, lead II is measured by calculating the potential difference of both electrodes by setting the right arm to the negative (−) pole and the left leg to the positive (+) pole. Reference numeral 633 of FIG. 6 represents a waveform of lead II. In the case of measurement 651 of lead III, lead III is measured by calculating the potential difference of both electrodes by setting the left arm to the negative (−) pole and the left leg to the positive (+) pole. Reference numeral 653 of FIG. 6 represents a waveform of lead III.

Figure 7:
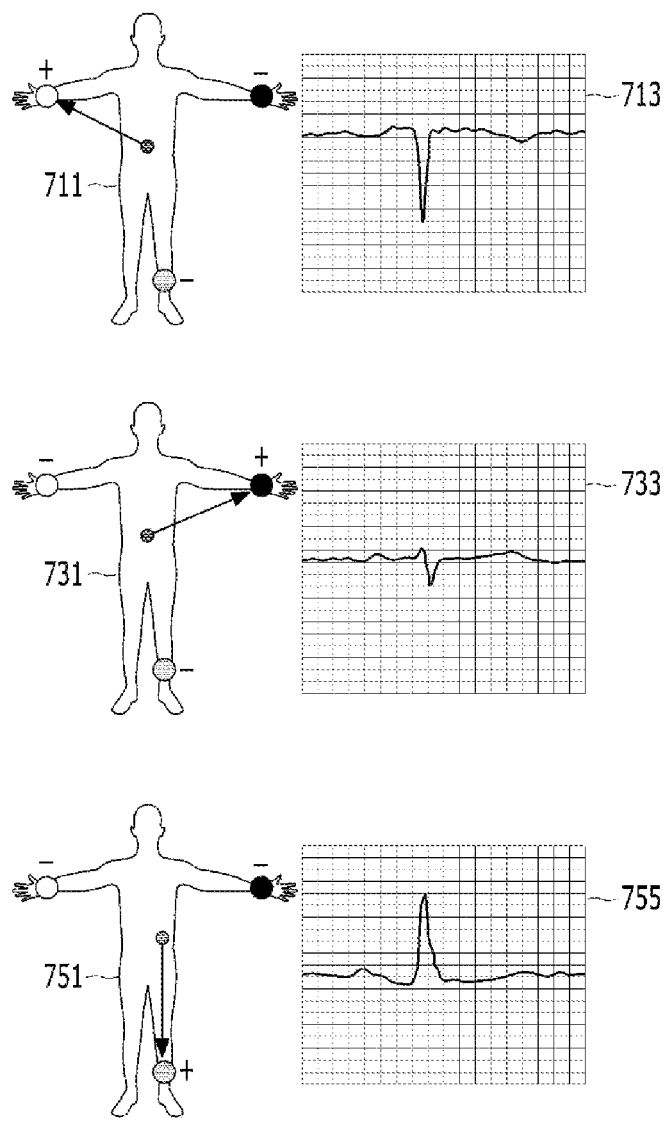
FIG. 7 is a diagram illustrating an amplification limb lead among the electrocardiogram leads that may be measured according to an embodiment of the present disclosure.

FIG. 7 is a diagram illustrating an amplification limb lead among the electrocardiogram leads that may be measured according to an embodiment of the present disclosure. Lead aVR is measured from the electrode connected to the right arm. In this case, an aVR ECG waveform 713 measured by a single pole is recorded by amplifying the received electrical signal. In measurement 711 of the aVR lead, in respect to a direction of the electrode, the right arm is maintained to the (+) pole, and the left arm and the left leg are maintained to the (−) pole. Lead aVL is measured from the electrode connected to the left arm. In this case, an aVL ECG waveform 733 measured by the single pole is recorded by amplifying the received electrical signal. In measurement 731 of lead aVL, in respect to the direction of the electrode, the left arm is maintained to the (+) pole, and the right arm and the left leg are maintained to the (−) pole. Lead aVF is measured from the electrode connected to the left leg. In this case, an aVF ECG waveform 735 measured by the single pole is recorded by amplifying the received electrical signal. In measurement 751 of lead aVF, in respect to the direction of the electrode, the left leg is maintained to the (+) pole, and the left arm and the right arm are maintained to the (−) pole.

Referring to FIGS. 6 and 7, when a plurality of leads are calculated instead of the single lead as described above, the processor 510 should calculate the leads by setting different symbols of electrodes which are attached to the same location. In an embodiment of the present disclosure, the processor 510 may measure the ECG based on the number of electrodes in the measurable state or an attachment position of electrodes. The ECG measurement may be performed for each type of ECG lead. For example, when the processor 510 determines that the electrodes attached to the right arm and the left arm are in the measurable state, the processor 510 may be determined to measure lead I. As another example, when the processor 510 determines that all of the electrodes attached to the right arm, the left arm, and the left leg are in the measurable state, the processor 510 may determine to measure all of lead I, lead II, lead III, lead aVR, lead aVL, and lead aVF. The above-described example is just an example, and does not limit the present disclosure.

The processor included in the portable ECG measuring device according to an embodiment of the present disclosure may determine whether each electrode is in the measurable state based on a quality of the electrical signal received from the electrode. The quality of the electrical signal may include, for example, at least one of a strength of the electrical signal, a waveform of the electrical signal, or an input time interval of the electrical signal.

The strength of the electrical signal which becomes the basis of the judgment of the quality of the electrical signal may mean a magnitude of a value of current or voltage. When there is no strength of the received electrical signal or the strength of the electrical signal is smaller than a predetermined threshold value, the processor may determine that the electrode receiving the corresponding electrical signal is in the non-measurable state and exclude the corresponding electrode from the ECG measurement.

The waveform of the electrical signal which becomes the basis of the judgment of the quality of the electrical signal may mean a shape in which the received electrical signal is changed. That is, when the processor receives a waveform which may not be measured from an electrical activity according to a human heart rate, the received waveform may be excluded from the ECG measurement. For example, when the skin of another animal other than a person is in contact with the electrode or when the surface of the electrode is in contact with a conductive material in which minute current flows to receive an electrical signal having a pulse, the processor may determine that the electrode receiving the corresponding electrical signal is in the non-measurable state based on the waveform of the electrical signal, and exclude the corresponding electrode from the ECG measurement.

The input time interval of the electrical signal which becomes the basis of the judgment of the quality of the electrical signal may mean a time interval between received signals. That is, even though an electrical signal with an abnormal strength is received, when the time term is irregular or the electrical signal is received at a time term to interrupt accuracy, the processor may not use the electrical signal during a computing process. For example, when the electrode is not in close contact with the skin of the user or the user intends to measure the ECG during a violent movement, such an abnormal electrical signal may be received.

As described above, in the present disclosure, the processor determines whether the ECG can be measured based on the quality of the corresponding electrical signal and then measures the ECG. This disclosure may derive a more accurate ECG measurement result. In addition, when the processor may not measure the ECG, the processor may inform the user about the cause in detail. An item regarding the quality of the electrical signal as an example does not limit the present disclosure In the present disclosure, the quality of the electrical signal may be determined by comprehensively considering several items which may be interpreted as noise of the electrical signal.

In embodiments of the present disclosure, the processor 510 included in the portable ECG measuring device may determine the type of ECG lead which is measurable according to the number of electrodes in the measurable state and/or the attachment position of electrodes. The processor 510 may determine whether each electrode is in the measurable state based on the quality of the electrical signal received from the electrodes as described above. Accordingly, according to the present disclosure, the processor 510 may determine the type of measurable ECG lead in response to the received electrical signal.

In embodiments of the present disclosure, the processor 510 included in the portable ECG measuring device may calculate a changed type of electrocardiogram lead based on a changed number of electrodes which is in the measurable state or a changed attachment position of the electrodes, when the number of electrodes in the measurable state or the attachment position of the electrodes changes during the electrocardiogram measurement. Specifically, when the processor 510 receives the electrical signal from the third electrode attached to the left leg (LL) during measuring ECG lead I recorded by the potential difference between the left arm (LA) and the right arm (RA), and determines that the third electrode is in the measurable state, the processor 510 may determine to measure an additional ECG lead. As another embodiment, when the third electrode is changed to the non-measurable state while the processor 510 determines that all of the first, second, and third electrodes are in the measurable state to measure an ECG lead corresponding to each electrode pair, the processor 510 may determine to continuously measure only lead I recorded by the electrical signal from the first and second electrodes. The portable ECG measuring device of the present disclosure determines whether each electrode is in the measurable state based on the quality of the electrical signal and when the number of electrodes in the measurable state or the attachment position of electrodes is changed, the portable ECG measuring device accordingly determines whether to measure what type of ECG lead, and as a result, multiple noise is included or the ECG lead itself is not calculated based on an unstable electrical signal. This consequently causes an inaccurate ECG lead not to be displayed to the user, thereby providing effect data so as to make an accurate clinical judgment. Hereinafter, the type of ECG lead for measurable electrode pairs will be described.

In embodiments of the present disclosure, when the number of electrodes in the measurable state is two, the ECG lead calculated by the processor 510 included in the portable ECG measuring device may be lead I if the attachment positions of two electrodes are the left arm (LA) and the right arm (RA), lead II if the attachment positions are the left leg (LL) and the right arm (RA), and lead III if the attachment positions are the left leg (LL) and the left arm (LA). Specifically, when the processor 510 determines that the first electrode attached to the left arm (LA) and the second electrode attached to the right arm (RA) are in the measurable state, the processor 510 may measure lead I which is the lead between the LA and the RA. As another embodiment, when the processor 510 determines that the third electrode attached to the left leg (LL) and the second electrode attached to the right arm (RA) are in the measurable state, the processor 510 may measure lead II which is the lead between the LL and the RA. As yet another embodiment, when the processor 510 determines that the third electrode attached to the left leg (LL) and the first electrode attached to the left arm (LA) are in the measurable state, the processor 510 may measure lead III which is the lead between the LL and the LA.

In embodiments of the present disclosure, when the number of electrodes in the measurable state is three, the ECG lead calculated by the processor 510 included in the portable ECG measuring device may include at least one of lead I, lead II, lead III, lead aVR, lead aVL, or lead aVF. Specifically, when the processor 510 determines that all of the first electrode of the left arm (LA), the second electrode of the right arm (RA), and the third electrode of the left leg (LL) are in the measurable state, the processor 510 may measure six leads including lead I, lead II, lead III, lead aVR, lead aVL, or lead aVF. Alternatively, the processor 510 may measure only some leads.

The type of measurable ECG lead described above is just an example, and may include all types of ECG leads which may be appreciated with reference to FIGS. 6 and 7 of this specification. Since the processor included in the portable ECG measuring device according to the present disclosure may determine the type of measurable ECG lead according to the number of electrodes in the measurable state and/or the attachment position of the electrode as described above, the processor may consecutively measure the ECG lead through computation type switching even though a specific electrode is added or removed. The present disclosure that measures the ECG lead with the number of electrodes in the measurable state apart from the number of attached electrodes has an advantage in that even though all electrodes required for measuring the ECG may not normally receive the electrical signal, a specific type of ECG result may be acquired based on currently received electrical signals.

When the sub measurement unit including the third electrode is stored in the main measurement unit, the processor 510 included in the portable ECG measuring device according to an embodiment of the present disclosure may determine that the third electrode is in the non-measurable state. As described above, the sub measurement unit may be stored and kept in one side of the main measurement unit. In this case, the processor 510 may recognize that the sub measurement unit is stored in the main measurement unit and determine that the third electrode is in the non-measurable state. In this case, the processor 510 may measure lead I based on the electrical signals received through the first and second electrodes included in the main measurement unit. When the processor 510 determines that the third electrode is in the non-measurable state only by a fact that the sub measurement unit is stored as described above, the processor 510 may more rapidly determine the number of measurable electrodes. If the processor 510 determines whether the electrode is in the measurable state only based on the quality of the received electrical signal, even when the sub measurement unit is stored in the main measurement unit and not used for ECG measurement, the processor 510 should wait for the electrical signal received from the sub measurement unit and furthermore, determine the quality of the electrical signal. This has a problem in that a delay of a measurement type is caused. On the contrary, if the sub measurement unit is stored in the main measurement unit according to the present disclosure, when the sub measurement unit determines that the third electrode is in the non-measurable state regardless of reception of the electrical signal, an ECG measurement speed of the processor 510 through the main measurement unit may increase and separate unnecessary data transmission and reception may be prevented.

The portable ECG measuring device according to an embodiment of the present disclosure may further include an output unit. The output unit may output at least one of information related to electrical signal measurement of each electrode, information related to an electrocardiogram measurement method of a processor, or user notification information. The output unit may include at least one of a component for voice output and a component for outputting a video or text. The information related to electrical signal measurement may include data regarding the quality of the electrical signal received from each electrode. For example, the information related to electrical signal measurement may include data for whether the strength of the electrical signal received from each electrode is excellent, the waveform of the electrical signal, or the time interval. Further, the information related to electrical signal measurement may include data for which electrode is in the measurable state according to a determination result for each electrode. The information related to the electrocardiogram measurement method may include, for example, the number or type of ECG leads currently measured due to the electrode in the measurable state. Specifically, when the electrode in the measurable state is the electrode attached to the right arm and the electrode attached to the left arm, the output unit may output that the currently measured ECG lead corresponds to lead °. The user notification information may include, for example, a notification regarding electrode reattachment, a notification regarding electrode attachment relocation, a notification for a warming notification measurement result for measurement while moving, or an emergency notification depending on a risk level of the measurement result. The output unit may be included in a separate terminal of the user interlocked with the portable ECG measuring device. The separate terminal of the user may include, for example, a PC, a smartphone, a tablet terminal, etc., of the user.

Figure 8:
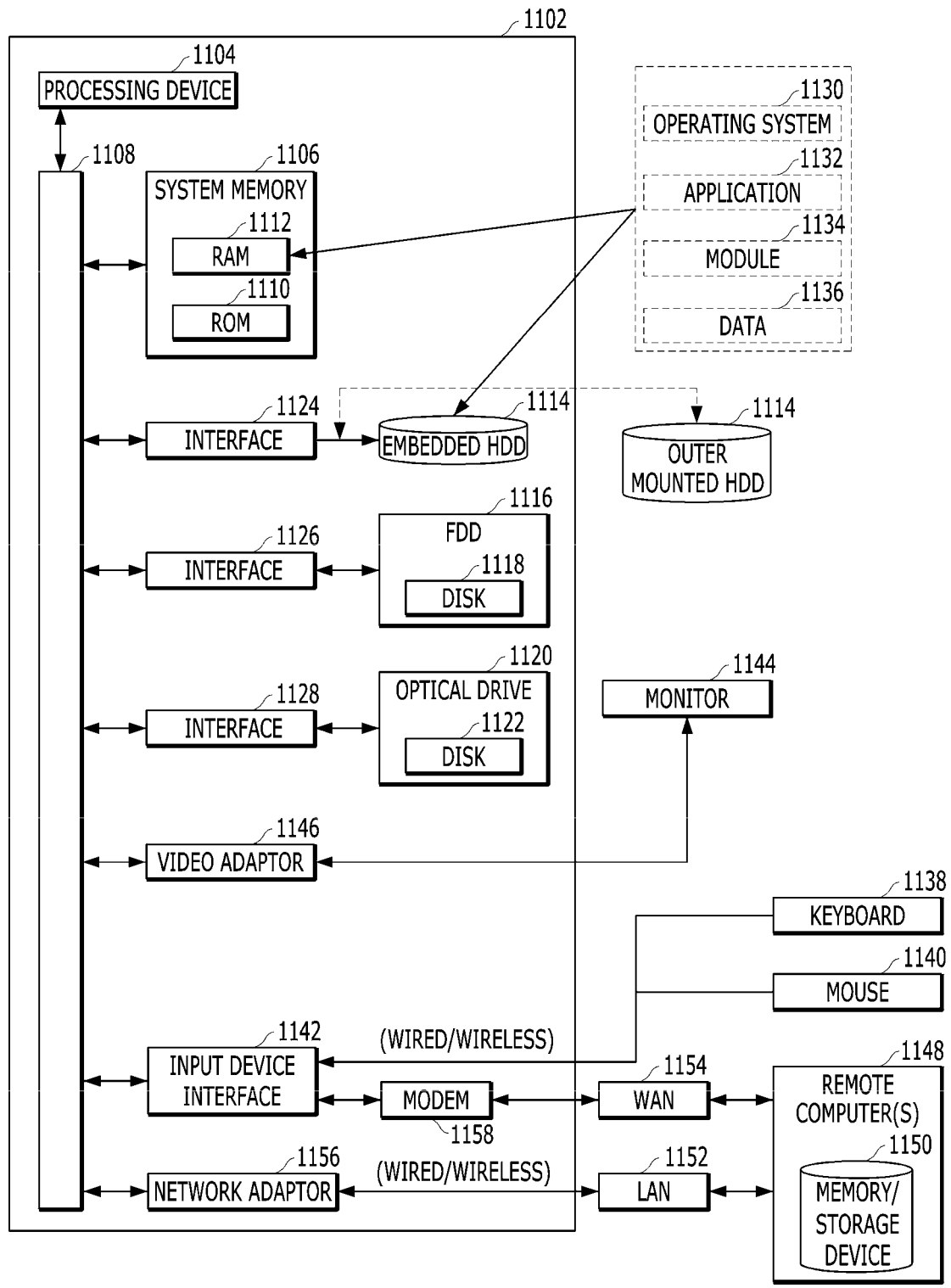
FIG. 8 is a simple and normal schematic view of a computing environment in which the embodiments of the present disclosure may be implemented.

FIG. 8 is a simple and normal schematic view of a computing environment in which the embodiments of the present disclosure may be implemented.

It is described above that the present disclosure may be generally implemented by the computing device, but it should be known that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The embodiments described in the present disclosure may also be implemented in a distributed computing environment in which predetermined tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, temporary and non-temporary media, and movable and non-movable media implemented by a predetermined method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined other media which may be accessed by the computer or may be used to store desired information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal acquired by configuring or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting. The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined data in an appropriate digital format. In the description of the computer readable media, the mobile optical media such as the HDD, the mobile magnetic disk, and the CD or the DVD are mentioned, but it should be noted that other types of media readable by the computer such as a zip drive, a magnetic cassette, a flash memory card, a cartridge, and others may also be used in an operating environment and further, the predetermined media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer(s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is and other means configuring a communication link among computers may be used.

The computer 1102 performs an operation of communicating with predetermined wireless devices or entities which are disposed and operated by the wireless communication, for example, the printer, a scanner, a desktop and/or a portable computer, a portable data assistant (PDA), a communication satellite, predetermined equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined technologies and techniques. For example, data, instructions, commands, information, signals, bits, symbols, and chips which may be referred in the above description may be expressed by voltages, currents, electromagnetic waves, magnetic fields or particles, optical fields or particles, or predetermined combinations thereof.

It may be appreciated by those skilled in the art that various logical blocks, modules, processors, means, circuits, and algorithm steps described in association with the embodiments disclosed herein may be implemented by electronic hardware, various types of programs or design codes (for easy description, herein, designated as software), or a combination of all of them. In order to clearly describe the intercompatibility of the hardware and the software, various components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various embodiments presented herein may be implemented as manufactured articles using a method, an apparatus, or a standard programming and/or engineering technique. The term manufactured article includes a computer program, a carrier, or a medium which is accessible by a predetermined computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but rather include all possible embodiments along with the full scope of equivalents to which such claims are entitled. Accordingly, the claims are not limited by the disclosure.

What is claimed is:

1. A portable electrocardiogram measuring device for calculating data from one or more electrocardiogram leads, the device comprising:
    a main measurement unit comprising a first electrode, a second electrode, and one or more processors; and
    a sub measurement unit comprising a third electrode;
    wherein the one or more processors measure an electrocardiogram, by receiving electrical signals from the first electrode, the second electrode, and the third electrode and by calculating different types of electrocardiogram leads based on the number of electrodes in a measurable state and an attachment position of the electrodes in the measurable state,
    wherein the one or more processors calculate data from a single electrocardiogram lead when only two electrodes are in the measurable state among the first electrode, the second electrode, and the third electrode,
    wherein the one or more processors calculate data from a plurality of electrocardiogram leads when the first electrode, the second electrode, and the third electrode are in the measurable state.

2. The portable electrocardiogram measuring device of claim 1, wherein the one or more processors determine whether each electrode is in a measurable state based on a quality of an electrical signal received from the electrodes.

3. The portable electrocardiogram measuring device of claim 2, wherein the quality of an electrical signal comprises at least one of a strength of the electrical signal, a waveform of the electrical signal, or an input time interval of the electrical signal.

4. The portable electrocardiogram measuring device of claim 1, wherein the third electrode is at least one of a dry type electrode or a wet type electrode.

5. The portable electrocardiogram measuring device of claim 1, further comprising one or more cables,
wherein the main measurement unit comprises one or more terminal inserting units for wired connection, and
the cable comprises a terminal for wired connection at one end, and the other end is connected to the sub measurement unit comprising the third electrode.

6. The portable electrocardiogram measuring device of claim 1,
wherein each of the main measurement unit and the sub measurement unit comprises a network unit for wireless data communication, and
the main measurement unit and the sub measurement unit wirelessly transmit and receive data.

7. The portable electrocardiogram measuring device of claim 1, wherein the sub measurement unit is capable of being coupled to one side of the main measurement unit through at least one of coupling by magnetic force, coupling by adhesive force, or fitting coupling.

8. The portable electrocardiogram measuring device of claim 1, wherein the main measurement unit is capable of storing the sub measurement unit.

9. The portable electrocardiogram measuring device of claim 1, wherein the one or more processors determine that the third electrode is in a non-measurable state, when the sub measurement unit comprising the third electrode is stored in the main measurement unit.

10. The portable electrocardiogram measuring device of claim 1, wherein the one or more processors calculate a changed type of electrocardiogram lead based on a changed number of electrodes which is in the measurable state or a changed attachment position of the electrodes, when the number of electrodes in the measurable state or the attachment position of the electrodes is changed during the electrocardiogram measurement.

11. The portable electrocardiogram measuring device of claim 1,
wherein, when the number of electrodes in the measurable state is two, the data from the electrocardiogram lead calculated by the one or more processors is
Lead I, when a location of two electrodes is in left hand (LA) and right hand (RA);
Lead II, when a location of two electrodes is in left foot (LL) and right hand (RA);
Lead III, when a location of two electrodes is in left foot (LL) and left hand (LA).

12. The portable electrocardiogram measuring device of claim 1, wherein, when the number of electrodes in the measurable state is three, the data from the electrocardiogram lead calculated by the one or more processors comprises at least one of lead I, lead II, lead III, lead aVR, lead aVL, or lead aVF.

13. The portable electrocardiogram measuring device of claim 1, further comprising an output unit, and
wherein the output unit outputs at least one of information related to electrical signal measurement of each electrode, information related to an electrocardiogram measurement method of a processor, or user notification information.

\* \* \* \* \*